United States Patent [19]
Schick et al.

[11] Patent Number: 5,995,583
[45] Date of Patent: *Nov. 30, 1999

[54] DENTAL RADIOGRAPHY USING AN INTRA-ORAL LINEAR ARRAY SENSOR

[75] Inventors: David B. Schick, Flushing; Daniel A. Neugroschl, New York; David B. Plass, Merrick; Jonathan Singer, Dobbs Ferry, all of N.Y.

[73] Assignee: Schick Technologies, Inc., Long Island City, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/748,954

[22] Filed: Nov. 13, 1996

[51] Int. Cl.$^6$ ........................................................ A61B 6/14
[52] U.S. Cl. ............................ 378/38; 378/98.8; 378/191
[58] Field of Search ............................... 378/38–40, 98.3, 378/98.8, 191, 190, 98.2

[56] References Cited

U.S. PATENT DOCUMENTS

| | | | |
|---|---|---|---|
| 4,057,733 | 11/1977 | Hofmockel et al. | 250/491 |
| 4,160,997 | 7/1979 | Schwartz | 358/93 |
| 4,179,100 | 12/1979 | Sashin et al. | 250/416 TV |
| 4,323,779 | 4/1982 | Albert | 250/401 |
| 4,409,616 | 10/1983 | Ledley | 358/111 |
| 4,593,400 | 6/1986 | Mouyen | 378/99 |
| 4,823,369 | 4/1989 | Guenther | 378/22 |
| 5,018,177 | 5/1991 | McDavid et al. | 378/62 |
| 5,179,579 | 1/1993 | Dove et al. | 378/38 |
| 5,331,166 | 7/1994 | Yamamoto et al. | 250/370.11 |
| 5,434,418 | 7/1995 | Schick | 250/370.11 |
| 5,471,515 | 11/1995 | Fossum et al. | 377/60 |
| 5,519,751 | 5/1996 | Yamamoto et al. | 378/98.8 |

FOREIGN PATENT DOCUMENTS

| | | |
|---|---|---|
| 0149502 | 7/1985 | European Pat. Off. . |
| 2701831 | 9/1994 | France . |
| 4218020 | 7/1993 | Germany . |
| 95/06434 | 3/1995 | WIPO . |

OTHER PUBLICATIONS

IEEE Transactions On Electron Devices, (undated), S. Mendis et al., "CMOS Active Pixel Image Sensor".

The Review of Scientific Instruments, vol. 50 (11), Nov. 1979, pp. 1415–1419, R.C. Gamble et al., "Linear Position–Sensitive X–ray Detector Incorporating a Self–scanning Photodiode Array".

*Primary Examiner*—Craig E. Church
*Attorney, Agent, or Firm*—Fitzpatrick, Cella, Harper & Scinto

[57] ABSTRACT

A method and apparatus for producing a X-ray image of a patient's teeth by placing an intra-oral sensor having a plurality of pixels disposed in a linear array inside the patient's mouth, and moving a radiation source around outside of the patient's mouth. The intra-oral sensor detects the radiation that has passed through the patient's teeth and generates corresponding output signals that depend on the amount of radiation arriving at each pixel. The information contained in the output signals is stored and can be used to create an X-ray image of the patient's teeth. The intra-oral sensor can be moved about inside the patient's mouth in coordination with the movement of the radiation source in order to improve the resulting image quality. This method and apparatus can be used to obtain an X-ray image of any number of teeth, including a panoramic image of all of the patient's teeth, in a single, quick, uninterrupted operation.

29 Claims, 5 Drawing Sheets

DENTAL RADIOGRAPHY USING AN INTRA-ORAL LINEAR ARRAY SENSOR

BACKGROUND OF THE INVENTION

This invention relates to a method and apparatus for obtaining an X-ray image of teeth. Specifically, the method and apparatus use an intra-oral (i.e. in-the-mouth) linear array sensor to detect radiation that originates from a radiation source outside the mouth, and create an image from the output of the sensor.

The procedure most commonly used by dentists to obtain radiographic images of the teeth, jaw structure or the like of patients produces what is called a periapical X-ray radiograph. In this known procedure, an X-ray film packet is inserted into the patient's mouth near the teeth or other anatomical structure to be imaged. The procedure makes use of an X-ray tube of the type which generates X-rays at a fixed point on an anode and in which the X-rays radiate out from that fixed point. The tube is provided with a shield cone which is directed at the film packet through the teeth or other structures to be imaged. Precise positioning of both the film packet and the shield cone is necessary to obtain useful X-ray images.

Although the conventional periapical X-ray procedure is very extensively used, it is subject to several serious disadvantages. The need to insert and retain a relatively large film packet in a patient's mouth, for example, often causes discomfort or gagging and may not be tolerable to certain patients such as small children and elderly persons. Further, no visible image is available to the dentist until the film packet has been removed and subjected to a time-consuming and costly development procedure. An instantaneous radiographic image would be much more useful to the dentist. In addition, this development procedure requires the use of chemicals which can have a negative environmental impact.

Another very serious problem with film is the undesirably large radiation dosage that is needed in order to produce a complete set of dental X-ray images. This is in part a result of the very low detection efficiency of the unscreened X-ray film commonly used for dental X-ray operations.

Techniques for reducing radiation exposure have heretofore been developed utilizing screened film that greatly improves detection efficiency by disposing an image-intensifying phosphorescent material on the X-ray film emulsion surface. The phosphorescent screen, however, reduces the definition of the resulting images, and has accordingly proved to be impractical in many situations.

The problem of high radiation exposure in dental radiology is often aggravated by a need to repeat the X-ray imaging process. For example, after the X-ray film is developed, it may be found that the film was not properly aligned during the original exposure, or that errors were made in developing the exposed X-ray film. Each of these occurrences is fairly common.

Some newer X-ray imaging systems do not use photographic film, and thereby avoid some of the disadvantages described above. For example, U.S. Pat. No. 4,160,997 (Schwartz), the pioneer patent in the field of filmless dental radiography, describes a system for taking periapical X-rays using an electronic sensor instead of photographic film. In Schwartz, X-rays which have passed through the patient's teeth are converted into light by a phosphorescent screen, and the light is detected by a two-dimensional solid state image pickup device such as a CCD (charge coupled device). The screen and the image pickup device are packaged together and connected to an electronic video display system. Improvements to this type of system are described in U.S. Pat. No. 5,434,418 (Schick).

Systems of the type described in Schwartz address some of the problems associated with conventional periapical X-ray systems described above. In particular, because electronic sensors that use phosphorescent screens are much more sensitive to X-ray radiation than photographic film, systems using these sensors can use a much smaller dosage of X-rays to register an image. In addition, because the output of the electronic sensor can be processed very rapidly by a micro-computer, the images are available immediately after the exposure is taken. Finally, no film developing chemicals are needed with these electronic sensor systems.

However, while the electronic sensor systems provide significant advantages over traditional photographic periapical systems, some disadvantages remain. Most notably, it is still necessary to insert the electronic sensor into the patient's mouth repeatedly, in various positions, and to take multiple exposures.

Because a full set of periapical X-rays includes up to 21 X-ray pictures, the process of asking the patient to open his mouth, inserting the film packet or electronic sensor, walking out of the room, actuating the X-ray tube, returning to the room, and repositioning the sensor must be repeated numerous times. Even when an abbreviated set of "bite wing" periapical X-rays are taken, the process must be repeated four times. This takes a significant amount of time, even when performed by a highly skilled technician, and can be even more time-consuming with a less experienced technician. In addition, the process is uncomfortable for the patient because biting down on the sensor package can be painful, and because the patient cannot speak for extended periods of time.

The panoramic (also known as pantomographic) image technique is another advance over standard periapical X-ray imaging, and has been extensively utilized in the recent past by dentists and oral surgeons. In this procedure, panoramic or wide angle X-ray images are produced by generating a narrow linear X-ray beam which is revolved during the exposure about an axis of rotation which passes through the anatomical structures to be examined. The X-ray tube is essentially a conventional one which generates X-rays at a small fixed point on an anode. Radiation generated at this point is collimated by a first slit which is parallel to the axis of rotation, passes through the patient's head and then through a second similar collimating slit situated in front of a screened film cassette which is rotated in synchronism with the rotational movement of the X-ray beam. The tube and detector motion causes the X-ray beam to sweep across the intervening anatomical structures. Upon development of the film, a panoramic two-dimensional strip image is produced of curved anatomical structures in the patient's head such as the mandible or maxilla.

Although a significant reduction of patient radiation dosage may be realized in comparison with periapical procedures, the conventional panoramic image technique is itself subject to several disadvantages. It is necessary that the X-ray beam pass through the entire skull of the patient, even if it is only desired to obtain an image of a portion of the skull such as the dental arch. Consequently unwanted images are superimposed upon the desired image data. This makes interpretation of the image more difficult and detracts from the general quality of the image by obscuring desired data to some extent with undesired information. Moreover, radiation exposure remains undesirably high as the X-ray beam must necessarily pass through the entire skull. Anatomical structures which are not of particular interest are thereby necessarily subjected to radiation dosage which does not contribute any useful information but actually detracts from the quality of the desired data. Further, a significant amount of X-ray scattering occurs during passage of the X-ray beam through the patient's entire head, creating a background fog in the image on the developed film that undesirably limits the range of contrast in the image and which may cause loss of definition. This process also requires the time consuming and troublesome film developing process of the conventional periapical X-ray procedure.

Additional losses of definition and contrast arise from the presence of the intensifying screen in front of the X-ray film. Underlying and supplementing these contrast limitations peculiar to the panoramic image technique is the undesirably limited grey scale latitude of X-ray film in general. Still further, a long exposure time, typically about 20 seconds, is needed to complete a full-mouth panoramic image. As result, problems often arise from patient motion or equipment vibration with consequent blurring of the resulting X-ray images. This tends to be particularly severe when the patient is an infant or young child. Finally, a considerable degree of distortion of the depicted objects is normally present in the conventional panoramic image.

Attempts have been made to develop a system that eliminates some of these shortcomings. U.S. Pat. No. 4,323,779 (Albert) describes a panoramic X-ray system that uses an electronic sensor instead of photographic film. In particular, Albert teaches the use of a sweeping electron beam to produce a moving point source of X-rays. The X-rays from this moving point source pass through the patient's teeth and strike an X-ray detector, which is made of a small scintillator crystal that converts the X-rays into visible light and a photosensitive element that converts the light into an electrical signal. As the point source is moved, the X-rays from the source will pass through different points on the patient's teeth on their way to the sensor. A portion of the X-rays is absorbed by the teeth, and the rest strikes the sensor. The electrical signal produced by the sensor is proportional to the portion of X-ray radiation that arrives at the sensor. This electrical signal is then processed by appropriate electronic circuitry.

Albert's system, however, has several drawbacks of its own. In particular, the system relies on complex components, including an electron gun, an anode plate, and a deflector means for moving the point X-ray source. Two problems are inherent in this type of system: Optical distortions must be compensated for, and focal length adjustments are often required. Moreover, the Albert system cannot provide an panoramic image of the entire mouth in one operation—it can only obtain an image of a portion of the dental arch. Therefore, multiple exposures are required in order to obtain a full panoramic X-ray image of the patient's teeth. Moreover, attempts to increase the number of teeth in a single image result in increased optical distortion.

There is therefore a need to develop a substantially improved dental radiography system that departs from past approaches.

SUMMARY OF THE INVENTION

It is accordingly a general object of the present invention to provide a new dental radiography system that takes an entirely fresh approach, departing significantly from the concepts and teachings of the prior art, in order to provide improved results.

Another object of the invention to obtain an image of any number of teeth in a patient's mouth, ranging from a single tooth to a complete panoramic image of all of the patient's teeth, in a single operation, without requiring multiple insertions of a radiation detector into the patient's mouth.

Another object of the invention is to obtain a high quality image free from various types of image degradation including (1) reduced image definition, which occurs when screened film is used; (2) optical distortion, which is inherent in scanning spot systems; and (3) superposed images of bony structures that obstruct the desired image of the teeth, which is a problem in panoramic dental X-rays systems where the radiation source and sensor are both located outside of the patient's head.

Other objects include (1) reducing the amount of time required to obtain an image of multiple teeth; (2) reducing discomfort to the patient; (3) reducing the amount of radiation to which the patient is exposed; and (4) eliminating the time consuming process of film developing and use of chemicals for film developing.

A first aspect of the present invention which achieves these objects relates to an apparatus for producing an X-ray image of a patient's teeth, and includes a radiation source which can be moved to a plurality of positions outside the patient's mouth, and a sensor, which is placed inside the patient's mouth, for detecting radiation. The sensor has a plurality of pixels disposed in a linear array (i.e. lined up adjacent to one another, single file, in a substantially straight line). The sensor generates output signals representing the amount of radiation that passes through the patient's teeth without being absorbed and arrives at each of the pixels. Information from the sensor that is received when the radiation source is located in various positions is stored on a storage medium, under control of appropriate electronic circuitry.

In another aspect of the present invention, the radiation source and collimator are replaced with a support member that is capable of supporting a radiation source in a plurality of positions outside the patient's mouth. This aspect of the invention is intended for use with an external radiation source.

In another aspect of the present invention, the sensor includes a plurality of scintillator elements disposed in a linear array, which convert radiation to light. An optical sensor with a plurality of light-sensitive sensing elements is used, with each of the light sensing elements being optically coupled to a scintillator element to detect the light produced by the associated scintillator element.

Yet another aspect of the present invention relates to a method of producing an X-ray image of a patient's teeth by placing a radiation sensor having a plurality of pixels inside a patient's mouth, and moving a radiation source to a plurality of positions outside the patient's mouth. Radiation from the source passes through the patient's teeth and strikes the radiation sensor. The radiation arriving at the sensor is detected by the sensor, which generates output signals representing the amount of radiation arriving at each of the pixels of the sensor. The information from the output signals is stored for at least some of the positions of the radiation source. This storing operation depends in part on the position of the radiation source.

Additional objects, advantages, and features of the invention will become apparent to those skilled in the art upon an examination of the following detailed description of preferred embodiments taken in conjunction with the accompanying drawings.

DETAILED DESCRIPTION OF THE PREFERRED EMBODIMENTS

Figure 1:
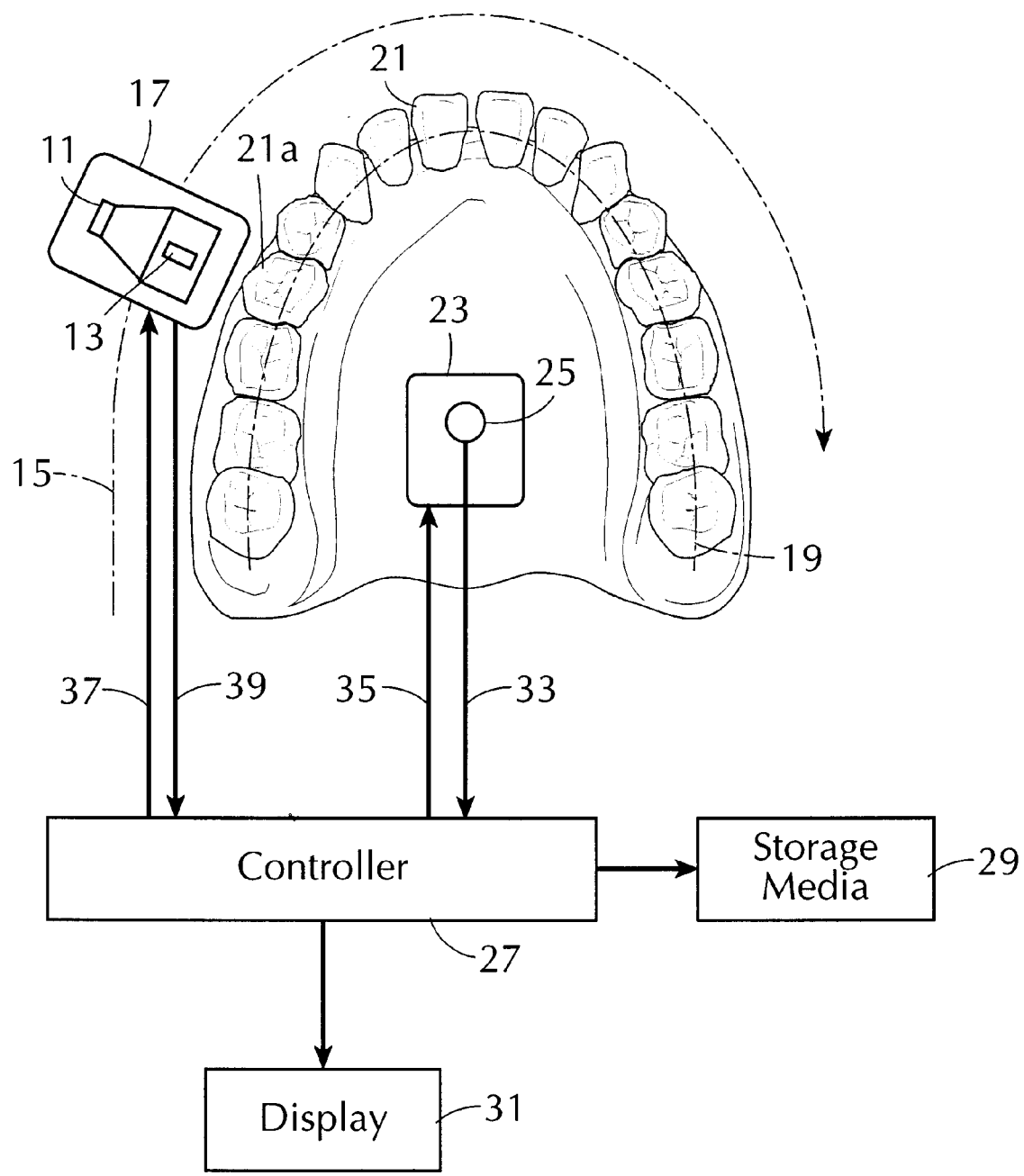
FIG. 1 is a diagrammatic representation of the panoramic X-ray imaging apparatus of the present invention.
Figure 4A:
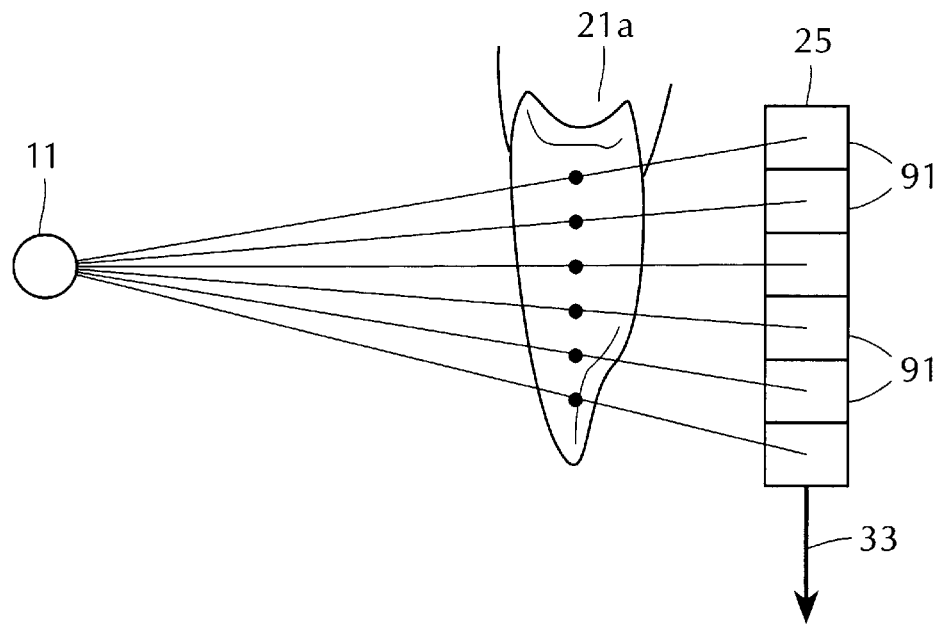
FIG. 4a depicts radiation passing through a tooth and arriving at the sensor.

Referring to FIG. 1, which depicts an embodiment of the present invention, a radiation source 11 is supported by a movable support member 17 located outside the patient's head. An intra-oral sensor 25 is placed inside the patient's mouth. Radiation from the radiation source 11 passes through a particular one of a patient's teeth 21a and strikes the sensor 25. As shown in FIG. 4a, the sensor contains a plurality of pixels 91 arranged in a linear array (i.e. the pixels are lined up adjacent to one another, single file, in a substantially straight line).

Figure 5:
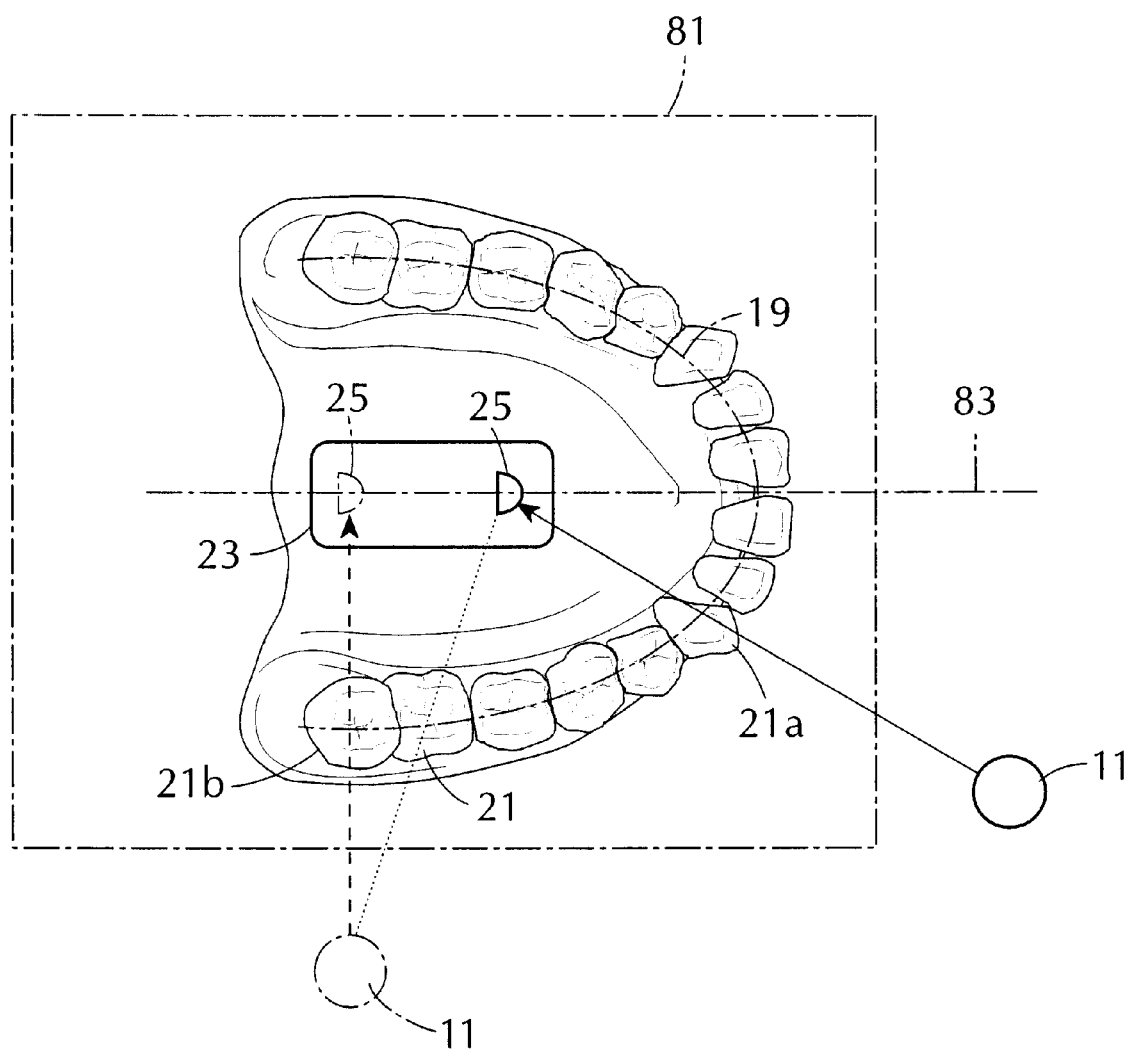
FIG. 5 depicts the placement of the sensor inside the patient's mouth.

FIG. 5 shows the plane 81 of the dental arch 19. The preferable orientation of the linear array is perpendicular to this plane, projecting out of the page. Returning to FIG. 4a, the radiation from the radiation source 11 passes through particular points on the tooth 21a and arrives at each of the pixels 91 of the sensor 25. As it passes through the tooth, some portion of the radiation will be absorbed by the tooth, the exact percentage depending upon the density of the tooth at that particular point. The amount of unabsorbed X-rays, therefore, corresponds to the density of the tooth.

The sensor generates output signals 33 that correspond to the amount of radiation arriving at each pixel, for each of the pixels in the sensor. This information corresponds to the density of the tooth for all of the points on the tooth 21a through which the radiation passed before it was detected by a particular pixel 91. Because the pixels in the sensor are arranged in a vertical linear array, as explained below, the points on the tooth 21a through which the radiation passed on the way to the respective pixels will define a substantially straight and substantially vertical line on the tooth, with the output of each pixel corresponding to the density of the tooth at each point on the line. Thus, the combined outputs of all the pixels describe the density of a "vertical slice" of the tooth 21a. Electronic circuitry in the controller 27, depicted in FIG. 1, stores the information of this vertical slice on the storage medium 29.

The radiation source 11 is then moved to a second position along a desired path 15. In this new position, the radiation passes through the next set of vertical points of the patient's tooth and arrives at the array of pixels. As before, some of the radiation will be absorbed by the tooth, depending on the density of the tooth at each new point. The points on the tooth through which the radiation passes on the way to the respective pixels will define a new vertical line on the tooth, and the output of each pixel will correspond to the density of the tooth at each point on the new line. Thus, the combined outputs of all the pixels describe the density of a second vertical slice of the tooth. The circuitry in the controller 27 stores the information of the second vertical slice on the storage medium 29.

This process of moving the radiation source along the desired path and storing the sensor information corresponding to a given vertical slice is repeated over and over, until the system has stored information about the entire region of interest of the patient's teeth on the storage medium 29. The system uses the stored information to create an image representing the density of the patient's teeth on display 31.

The radiation source 11 can be a X-ray tube, of the type conventionally used in dentists' offices, such as the model 7/70 tube made by Gendex. The radiation source can also be a radioactive material. If a radioactive material is used, proper precautions must of course be provided in order to protect the patient and the technician from exposure to radiation. These precautions can include a shielding material that absorbs radiation, such as lead, that surrounds the radioactive material on all sides, with a shuttered opening on one side. When the shutter is opened, radiation from the material can escape through the opened shutter.

Because radiation can be dangerous to people, it is desirable to reduce the patient's exposure to radiation. Therefore, regardless of the type of radiation source selected, a collimator 13 may be placed between the radiation source and the patient. The collimator blocks some or all of the radiation that is not aimed directly at the sensor in the patient's mouth. This has no effect on the image because only the radiation that arrives at the sensor contributes to the image. The collimator can be as simple as a metal plate that blocks X-rays with a slot in the plate to allow the X-rays to pass out in a particular direction. It can instead be made of lead glass with a plurality of small holes, as described in Albert. Many other collimator configurations can also be used, as will be understood by those skilled in the art.

The path 15 that the radiation source 11 follows about the patient's head is selected so that the radiation emerging from the radiation source will pass through the teeth 21 substantially perpendicular to the patient's dental arch 19, and parallel to the plane of the dental arch, as illustrated in FIG. 5. A single path is sufficient for use with all patients for most purposes. The path can also be custom fit to a particular patient. Alternatively, a set of predefined paths may be used for particular situations. For example, a selection of two paths for small and large mouths may be used.

Returning to FIG. 1, the movable support member 17 guides the radiation source 11 along the desired path 15 about the patient's head. It is preferable for the radiation source 11 to remain aimed at the radiation sensor 25 that is located inside the patient's mouth as the radiation source is moved.

The movable support member 17 may be operated automatically or manually. It may move the radiation source 11 under control from controller 27, or it may operate independently. If the controller 27 controls the movement of the radiation source 11 by, for example, sending signals 37 to the movable support member 17, then the controller 27 can determine the position of the radiation source 11 at any given time by keeping track of those signals 37. This information will be used when the sensor information is stored. Alternatively, the controller 27 can detect the position of the radiation source 11 by receiving signals 39 that inform the controller of the radiation source's position. As another alternative, the controller can determine the position of the radiation source 11 by receiving signals 39 from which the position can be derived, such as the velocity or acceleration of the radiation source. The controller 27 interprets these signals to determine the position of the radiation source 11, which will be used when the sensor information is stored. The particular type of movable support member 17 selected is not critical, as long as it can move the radiation source 11 along the desired path 15, the radiation source 11 remains aimed at the sensor 25, and the controller 27 always has accurate information as to the position of the radiation source 11 when it is moved.

Figure 2:
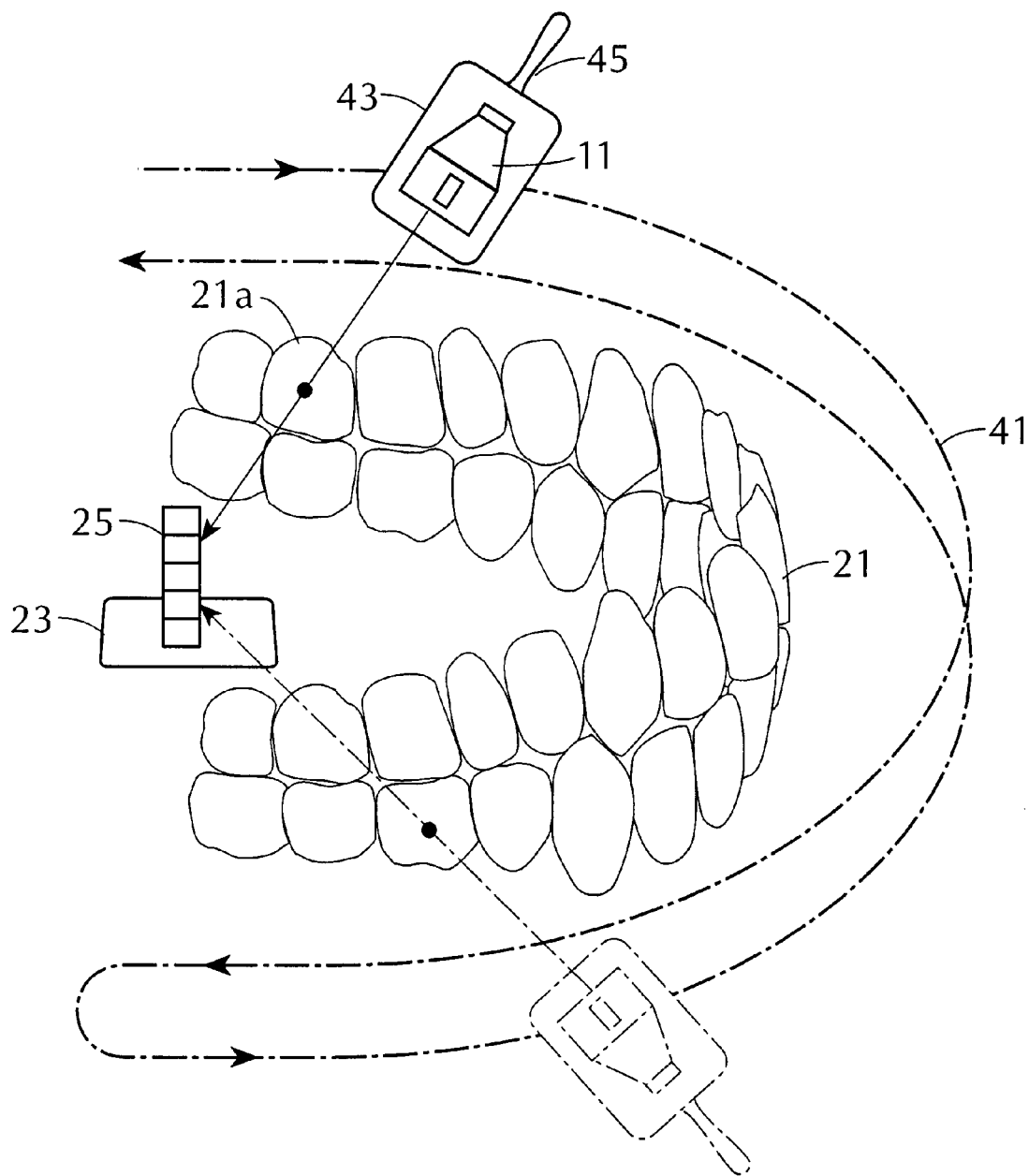
FIG. 2 is a perspective representation of the X-ray imaging apparatus of FIG. 1.

Referring to FIG. 2, one appropriate type of movable support member is a manually operated system with a fixed track 41 and a platform 43 that slides or rolls along the track 41. The radiation source 11 is mounted on the platform 43. The platform 43 also has a handle 45, which the operator uses to move the platform from the start of the track 41 to the end of the track. Another appropriate movable support member also uses a track and a sliding or rolling platform and automates the movement of the radiation source. The movement may be powered by a motor that drives the platform along the track. Hydraulics, pneumatics, spring power, or gravity can also be used to drive the platform.

Returning to FIG. 1, one alternative arrangement uses a movable arm (not illustrated) to support the radiation source 11. The radiation source 11 is moved along the path 15 by one or more actuators (not illustrated), such as motors. The system is controlled by the controller 27. Once again, the specifics of the movable support member are not critical, as long as the radiation source 11 can be moved along the desired path, the radiation source remains aimed at the sensor 25, and the controller 27 always has accurate information as to the position of the radiation source 11.

A radiation sensor 25 is placed inside the patient's mouth. Referring now to FIG. 4a, the sensor has a plurality of pixels 91 disposed in a linear array. The preferred axis for the linear array is vertical (i.e. perpendicular to the plane of the dental arch). This preferred axis projects out of the page in FIGS. 1 and 5. Returning to FIG. 4a, when the linear array is oriented along the preferred axis, the radiation arriving at each of the pixels 91 in the sensor 25 will have passed through a series of points on the tooth 21a that make up a vertical line on the tooth 21a. Each of the pixels generates an output in response to the amount of incident radiation. Because the radiation arriving at the sensor 25 is proportional to the density of the points on the tooth 21a through which the radiation passed, the sensor outputs represent information about the density of the tooth along a vertical slice of the tooth. Variations from the preferred axis are acceptable, although system performance may be degraded as the deviation from the preferred axis increases.

Figure 4B:
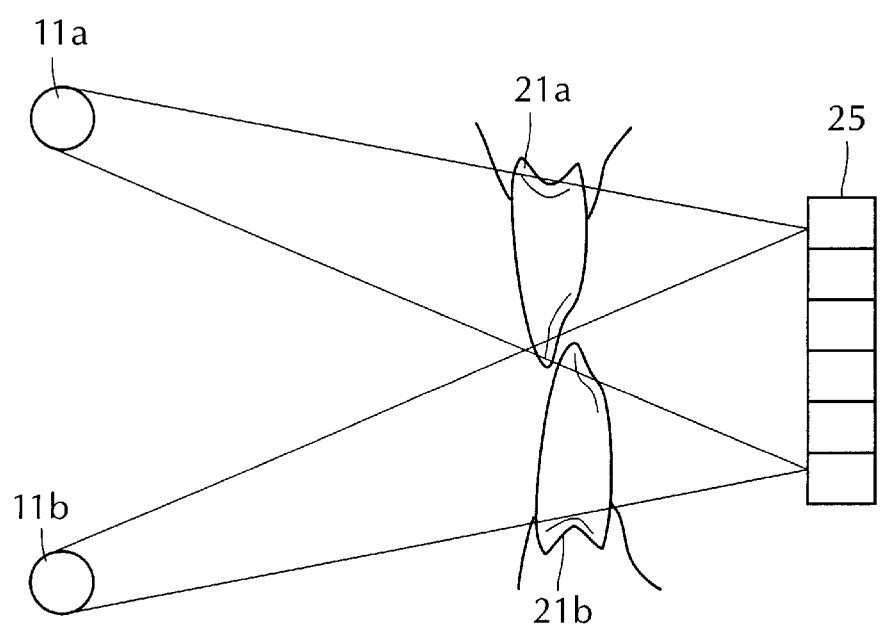
FIG. 4b depicts a dual source configuration, and radiation passing through upper and lower teeth.

By using two radiation sources mounted on the same movable support member, the path of the movable support member can be dramatically simplified. FIG. 4b shows how two radiation sources 11a, 11b can be used with a single sensor 25. The upper source 11a is used to illuminate the upper teeth 21a with radiation, and the lower source 11b is used to illuminate the lower teeth 21b. Both sources are preferably mounted on the same movable support member. With this dual source configuration, the path of the support member can be a simple arc or parabola, and the path can be confined to a single plane. When the upper source 11a is turned on, the sensor output 33 will correspond to a vertical slice of an upper tooth 21a. When the lower source 11b is turned on, the sensor output will correspond to a vertical slice of a lower tooth 21b. An equivalent arrangement would be a single radiation source with two output ports, along with a switching mechanism to send the radiation out of either one port or the other.

The sensor may be a solid state device that responds directly to the radiation arriving from the radiation source.

Figure 3A:
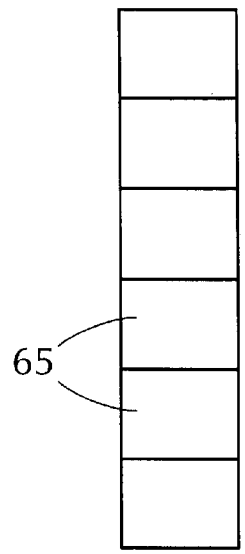
FIG. 3a is a diagrammatic representation of one embodiment of an intra-oral sensor of the present invention.

FIG. 3a is a schematic representation of this type of sensor, which consists of a plurality of radiation sensing pixels 65 lined up adjacent to one another, single file, in a substantially straight line. These pixels 65 produce an electrical output when struck by X-ray radiation.

Examples of suitable radiation sensing pixels include photodiodes, CCD cells, and CMOS active pixels. With CCD cells and CMOS active pixels, an electrical charge changes in proportion to the radiation arriving at a pixel. With photodiodes, a current is produced in proportion to the radiation arriving at a pixel. Appropriate electronic circuitry detects these electrical properties.

CCD devices are described in Schwartz's U.S. Pat. No. 4,160,997 and in the references incorporated therein, all of which are incorporated herein by reference. CMOS active pixels are described Fossum's U.S. Pat. No. 5,471,515, which is incorporated herein by reference. Photodiodes are described "Linear Position-Sensitive X-ray Detector Incorporating a Self-Scannning Photodiode Array", by R. C. Gamble et al., published in The Review of Scientific Instruments, Vol. 50(11), November 1979, which is also incorporated herein by reference.

Alternatively, the sensor may include a converter that converts the incident radiation into a different type of energy, and then detects the converted energy. For example, incident X-rays can be converted to visible light energy by a scintillator such as a phosphor screen composed of gadolinium oxysulfide powder. Scintillator crystals, such as sodium iodide doped with thallium, bismuth germinate or calcium fluoride may also be used. The light energy produced by the scintillator can then be detected by a photodiode, a CCD cell, or a CMOS active pixel, as describe above.

Figure 3B:
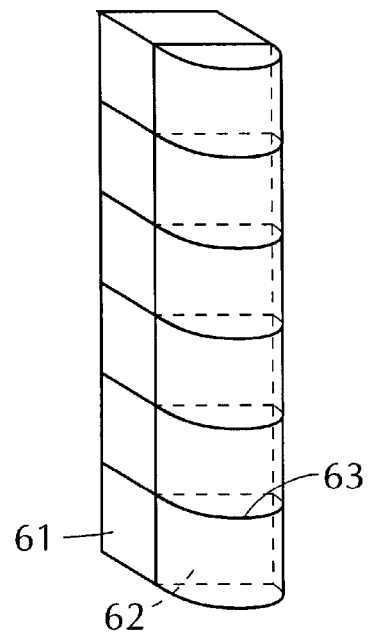
FIG. 3b is a diagrammatic representation of a second embodiment of an intra-oral sensor.

FIG. 3b is a schematic representation of this type of sensor. Radiation from the radiation source arrives at the sensor, having passed through the subject's teeth. When the radiation strikes the scintillator element 62, the scintillator element emits light. The light from the scintillator element 62 is detected by the light-sensitive sensing elements 61. Optimally, the entire system is matched so that the scintillator element 62 is highly responsive to the frequency of radiation emitted by the radiation source 11, and the light-sensitive sensing element 61 is highly responsive to frequency of light emitted by the scintillator element 62. The particular frequency of scintillation is not critical, and it can be within or beyond the spectrum of visible light.

The outer surface of the scintillator elements 62 can be convex, which helps the scintillator to respond to light arriving from various angles. The surface of the scintillator elements can also be shaped like slices of a partial cylinder, as depicted in FIG. 3b. Shields 63 may also be used between adjacent scintillator elements 62 to prevent a given light-sensitive sensing element 61 from detecting light from neighboring scintillator elements 62. The shields 63 are appropriately shaped to match the shape of the scintillator elements 62. For example, semicircular shields would be appropriate for half-cylinder shaped scintillator elements.

Figure 3C:
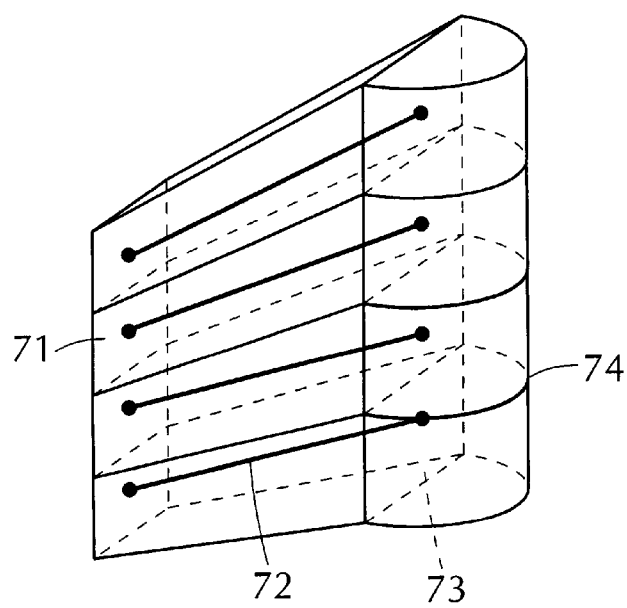
FIG. 3c is a diagrammatic representation of a third embodiment of an intra-oral sensor.

The scintillator elements 62 shown in FIG. 3b can be bonded to the light-sensitive sensing elements 61 with an optically transmissive material, or they can be held in place next to each other mechanically. An alternate configuration is shown in FIG. 3c, in which the light from a given scintillator element 73 is routed to the associated light-sensitive sensing element 71 by a fiber optic element 72. Convex or sliced-partial-cylinder scintillators may be used in this embodiment as well. Here again, the shields 74 are appropriately shaped to match the shape of the scintillator elements. For example, a rectangular shield with a semicircular end would be appropriate for the scintillator elements depicted in FIG. 3c.

Returning to FIG. 1, the sensor generates output signals 33. The output signals 33 contain information about the amount of radiation that has arrived at each pixel in the sensor during a given time. As explained above, because the radiation arriving at the sensor 25 is proportional to the density of the points on the tooth 21a through which the radiation passed, the sensor output represents information about the density of the tooth along a vertical slice of the tooth.

The format of the output signals 33 will vary, depending on the type of sensor 25 that is used. For example, if a linear array of individual photodiodes is used as the sensor, and all of the photodiode anodes are tied together, with an independent output lead available for each diode, then each output lead will contain a single output signal corresponding to the radiation arriving at a particular photodiode during the relevant time (which will correspond to the density of the tooth at one point). If the sensor is a CCD comprising a linear array of CCD cells, then the output signals will appear in sequence on a single output line as the information is shifted out of the CCD.

Appropriate circuitry within controller 27 is used to capture the information output from the sensor 25. The specific circuitry used will depend on the type of sensor selected, and on the way the pixels in the sensor are interconnected. Circuitry for performing this function is well known in the art of image processing. One example of this type of circuitry is the Datel 414 circuit card, which is designed for use in an IBM PC compatible computer. Datel Inc. is located at 11 Cabot Blvd., Mansfield, Mass. 02048.

Once the sensor output information is captured by the appropriate electronic circuit in the controller 27, it can be stored on the storage medium 29. The controller may be custom designed, or a general purpose computer (such as an IBM PC compatible computer) running a program designed for this purpose. Suitable programs are typically supplied by the circuit card manufacturer. The storage medium 29 can be optical, magnetic (such as magnetic core, tape, or disk), electronic (such as RAM or PROM), or of a mixed type. Other storage media, such as photographic film, mechanical, chemical, or biological systems can also be used. Electronic circuitry in the controller 27 appropriate for the selected type of storage medium 29 will control the storage of the sensor information on the storage medium 29. The process of storing the sensor information is also well known in the art of image processing.

After the sensor information has been stored, the entire process begins again. The radiation source 11 is moved to a new location; the radiation passes through a different vertical slice of the patient's teeth 21 on the way to the sensor 25; the sensor 25 generates outputs, and the sensor information is stored. These steps are repeated over and over again until information representing the entire desired image is stored on the storage medium 29.

With the dual radiation source configuration shown in FIG. 4b, similar processes can be used. For example, the imaging can be performed in a back-and-forth pass by first turning on the upper radiation source 11a and moving the radiation sources 11a, 11b in one direction while obtaining an image of the upper teeth 21a. Then, the lower source 11b can be turned on, and the sources 11a, 11b can be moved in the opposite direction while obtaining an image of the lower teeth 21b. Alternatively, the entire imaging process can be done in a one direction pass by first turning on the upper source 11a momentarily to obtain an image of a vertical slice of an upper tooth 21a, and then, without moving the sources, turning on the lower source 11b momentarily to obtain an image of a vertical slice of a lower tooth 21b. After the upper an lower slices are imaged, the radiation sources 11a, 11b are moved to their next position. This process is repeated until the entire desired image is stored.

The sensor information is stored in a way that preserves the relationship between each vertical slice of sensor information and the position of the radiation source 11 corresponding to that slice of sensor information. As one example, a word that describes the radiation source position can be written to the storage medium together with the sensor information. As another example, each slice of sensor information can be stored in a particular location within the storage medium, using either relative or absolute addressing. This enables image processing circuitry to reconstruct an image from the stored information.

Finally, the image processing circuitry combines all of the individual vertical image slices into a single composite image of the entire tooth (or group of teeth) that is being imaged. The image processing circuitry for accomplishing this is also well known in the art. The composite image can be displayed on display 31 in ways that are also well known in the art.

The number of vertical image slices that are combined by the electronic circuitry will affect the resolution of the resulting image. For example, to achieve a resolution of 50 dpi (dots per inch), 50 vertical slices must be combined for every horizontal linear inch of teeth being imaged. The resolution can be increased by increasing the number of vertical slices per horizontal linear inch. However, beyond a certain point, increasing the number of vertical image slices will not increase the resolution of the final image, because the finite size of the sensor pixels 61 limits the maximum resolution that can be attained.

Referring now to FIG. 5, it is preferable when the radiation travelling from the radiation source 11 to the sensor 25 passes through the patient's teeth 21 perpendicular to the patient's dental arch 19. This is particularly important when obtaining an image of the portion of a tooth that touches an adjacent tooth. To insure that the radiation impinges on the sensor 25 perpendicularly for all positions of the radiation source, the sensor is moved inside the patient's mouth in coordination with the movement of the radiation source. FIG. 5 shows, using solid lines, how the sensor 25 is located in a first position when the radiation source 11 is in a first position, and that the radiation arriving at the sensor 25 from the radiation source 11 passes through tooth 21a perpendicular to the dental arch 19. FIG. 5 also shows, using dashed lines, how the sensor 25 is located in a second position when the radiation source 11 is in a second position, and that the radiation arriving at the sensor 25 from the radiation source 11 also passes the edge of tooth 21b perpendicular to the dental arch 19. If the sensor 25 is not moved to the second position when the radiation source 11 is moved to its second position, then the radiation arriving at the source would not be perpendicular to the dental arch 19, as indicated by the dotted line.

The desired perpendicularity can be maintained by moving the sensor back and forth along a straight path on the line 83 that bisects the right side of the patient's teeth from the left side of the teeth. If the radiation sensor 25 is sensitive to radiation arriving from a sufficiently wide angle, then this linear motion would be sufficient to insure that the sensor 25 remains responsive to the radiation for all positions of the radiation source 11. Using a convex scintillator or the sliced-partial-cylinder shape scintillator as described above would increase the responsiveness of the detector to radiation arriving through the side of the patient's mouth. The sensor 25 can also be rotated as it is moved from one position to another, so that the sensor 25 is always facing toward the radiation source 11 to improve the responsiveness of the sensor 25 to radiation arriving through the side of the patient's mouth.

The mechanism for moving the sensor back and forth, and optionally for rotating the sensor, can be implemented using an electrical, mechanical, hydraulic or other system. As with the movable support member, which moves the radiation source, the specific structure for implementing the movable sensor support member is not critical, as long as the desired translation and rotation can be accomplished.

Arranging the pixels adjacent to one another as described, single file, in a substantially straight line provides a benefit over sensors using two-dimensional arrays of pixels because it (1) reduces the probability of scattered radiation striking an active section of the detector; (2) reduces the diffusion of light from the scintillator from one pixel to neighboring pixels; (3) simplifies processing of the sensor output that is generated as the radiation source is moved; and (4) enables convex scintillators to be used to enhance the sensor's response to light arriving from various angles.

While the present invention has been described above in terms of specific embodiments, it is to be understood that the invention is not limited to the disclosed embodiments. On the contrary, the present invention is intended to cover various modifications and equivalent structures included within the spirit and scope of the appended claims.

What is claimed is:

1. An apparatus for producing a panoramic X-ray image of a patient's teeth, comprising:
   a radiation source;
   a movable support member for supporting said radiation source in at least fifty positions outside the patient's mouth and moving said radiation source to the at least fifty positions;
   an intra-oral sensor for detecting radiation comprising a plurality of pixels disposed in a linear array, said sensor generating output signals representing sensor information corresponding to the amount of radiation arriving at each of the pixels for at least fifty vertical image slices, wherein each of the at least fifty vertical image slices corresponds to a respective one of the at least fifty positions of said radiation source;
   a storage medium for storing the sensor information for the at least fifty vertical image slices in a manner that preserves the relationship between each of the at least fifty vertical image slices and the corresponding one of the at least fifty positions of said radiation source; and
   image processing circuitry that combines each of the at least fifty vertical image slices into a single composite panoramic image.

2. An apparatus according to claim 1, further comprising a radiation collimator disposed between said radiation source and the patient to absorb radiation from said radiation source that is not directed towards said sensor.

3. An apparatus according to claim 1, further comprising:
   a radiation collimator disposed between said radiation source and the patient to absorb radiation from said radiation source that is not directed towards said sensor; and
   a movable sensor support member for supporting said sensor and moving said sensor in coordination with movements of said radiation source so that radiation traveling from said radiation source to said sensor passes through the patient's teeth substantially perpendicular to a dental arch of the patient,
   wherein said pixels comprise at least one of photodiodes, CCD cells and CMOS active pixels,
   wherein said storage medium comprises at least one of magnetic media, electronic media, and optical media, and
   wherein said radiation source comprises at least one of a radioactive material and an X-ray tube.

4. An apparatus according to claim 1, further comprising a second radiation source, supported by said movable support member, and circuitry for activating a desired radiation source.

5. An apparatus according to claim 1, further comprising a display for displaying an image representing the stored sensor information.

6. An apparatus according to claim 1, wherein said electronic circuitry controls the position of said radiation source.

7. An apparatus according to claim 1, wherein said electronic circuitry detects the position of said radiation source.

8. An apparatus according to claim 1, wherein said pixels comprise at least one of photodiodes, CCD cells and CMOS active pixels.

9. An apparatus according to claim 1, wherein said storage medium comprises at least one of magnetic media, electronic media, and optical media.

10. An apparatus according to claim 1, wherein said radiation source comprises at least one of a radioactive material and an X-ray tube.

11. An apparatus for producing a panoramic X-ray image of a patient's teeth, comprising:
    means for providing radiation;
    means for supporting said radiation-providing means in at least fifty positions outside the patient's mouth and moving said radiation-providing means to the at least fifty positions;
    means for detecting radiation comprising a plurality of pixels disposed in a linear array, and for generating output signals representing the amount of radiation arriving at each of the pixels for at least fifty vertical image slices, wherein each of the at least fifty vertical image slices corresponds to a respective one of the at least fifty positions of said radiation-providing means;
    means for storing information corresponding to the output signals for the at least fifty vertical image slices;
    means for controlling the storing of the information on said information-storing means, for the at least fifty vertical image slices, in a manner that preserves the relationship between each of the at least fifty vertical image slices and the corresponding one of the at least fifty positions of said radiation-providing means; and
    processing means for combining each of the at least fifty vertical image slices into a single composite panoramic image.

12. An apparatus for producing a panoramic X-ray image of a patient's teeth, the apparatus comprising:
    a movable support member upon which a radiation source is mounted, capable of supporting the radiation source in at least fifty positions outside the patient's mouth and moving the radiation source to the at least fifty positions;

an intra-oral sensor for detecting radiation comprising a plurality of pixels disposed in a linear array, said sensor generating output signals representing sensor information corresponding to the amount of radiation arriving at each of the pixels for at least fifty vertical image slices, wherein each of the at least fifty vertical image slices corresponds to a respective one of the at least fifty positions of the radiation source;

a storage medium for storing sensor information for the at least fifty vertical image slices in a manner that preserves the relationship between each of the at least fifty vertical image slices and the corresponding one of the at least fifty positions of the radiation source; and image processing circuitry that combines each of the at least fifty vertical image slices into a single composite panoramic image.

13. An apparatus according to claim 12, further comprising a display for displaying an image representing the stored sensor information.

14. A method of producing a panoramic X-ray image of a patient's teeth, comprising the steps of:

placing an intra-oral radiation sensor comprising a plurality of pixels disposed in a linear array inside a patient's mouth;

moving a radiation source to at least fifty positions outside the patient's mouth in sequence;

allowing radiation from the source to pass through the patient's teeth and strike the radiation sensor;

detecting radiation arriving at the sensor;

generating output signals representing sensor information corresponding to the amount of radiation arriving at each of the plurality of pixels of the sensor for at least fifty vertical image slices, wherein each of the at least fifty vertical image slices corresponds to a respective one of the at least fifty positions of said radiation source;

storing the sensor information for the at least fifty vertical image slices in a manner that preserves the relationship between each of the at least fifty vertical image slices and the corresponding one of the at least fifty positions of the radiation source; and combining each of the at least fifty vertical image slices into a single composite panoramic image.

15. The method according to claim 14, wherein the radiation source is moved together with a second radiation source, and further comprising the step of activating a desired radiation source.

16. An apparatus for producing a panoramic X-ray image of a patient's teeth, comprising:

a radiation source;

a movable support member for supporting said radiation source in at least fifty positions outside the patient's mouth and moving said radiation source to the at least fifty positions;

a intra-oral sensor comprising:

a plurality of scintillator elements disposed in a linear array, for converting incident radiation into light, and an optical sensor for detecting light, having a plurality of light-sensitive sensing elements, each of said sensing elements being optically coupled to a scintillator element, for generating output signals representing sensor information corresponding to the amount of radiation arriving at each of said scintillator elements for at least fifty vertical image slices, wherein each of the at least fifty vertical image slices corresponds to a respective one of the at least fifty positions of said radiation source;

a storage medium for storing the sensor information for the at least fifty vertical image slices in a manner that preserves the relationship between each of the at least fifty vertical image slices and the corresponding one of the at least fifty positions of said radiation source; and image processing circuitry that combines each of the at least fifty vertical image slices into a single composite panoramic image.

17. An apparatus according to claim 16, further comprising:

a radiation collimator disposed between said radiation source and the patient to absorb radiation from said radiation source that is not directed towards said sensor; and a movable sensor support member for supporting said sensor and moving said sensor in coordination with movements of said radiation source so that radiation traveling from said radiation source to said sensor passes through the patient's teeth substantially perpendicular to a dental arch of the patient, wherein said sensing elements comprise at least one of photodiodes, CCD cells and CMOS active pixels, wherein said storage medium comprises at least one of magnetic media, electronic media, and optical media, and wherein said radiation source comprises at least one of a radioactive material and an X-ray tube.

18. An apparatus according to claim 16, wherein said radiation source comprises at least one of a radioactive material and an X-ray tube.

19. An apparatus according to claim 16, further comprising a radiation collimator disposed between said radiation source and the patient to absorb radiation from said radiation source that is not directed towards said sensor.

20. An apparatus according to claim 16, wherein said storage medium comprises at least one of magnetic media, electronic media, and optical media.

21. An apparatus according to claim 16, further comprising a second radiation source, supported by said movable support member, and circuitry for activating a desired radiation source.

22. An apparatus according to claim 16, further comprising a display for displaying an image representing the stored sensor information.

23. An apparatus according to claim 16, further comprising a plurality of shields for optically isolating each sensing element from light that does not originate from the scintillator element to which the sensing element is optically coupled.

24. An apparatus according to claim 16, wherein each of said scintillator elements has a convex outer face for receiving incident radiation.

25. An apparatus according to claim 16, wherein said sensing elements are optically coupled to the scintillator elements with fiber optics.

26. An apparatus according to claim 16, wherein said sensing elements are bonded to said scintillator elements.

27. An apparatus according to claim 16, wherein said electronic circuitry controls the position of said radiation source.

28. An apparatus according to claim 16, wherein the electronic circuitry detects the position of said radiation source.

29. An apparatus according to claim 16, wherein said sensing elements comprise at least one of photodiodes, CCD cells and CMOS active pixels.

* * * * *